(12) United States Patent  
Georgeson et al.

(10) Patent No.: US 7,649,976 B2  
(45) Date of Patent: Jan. 19, 2010

(54) SYSTEM AND METHOD FOR DETERMINING DIMENSIONS OF STRUCTURES/SYSTEMS FOR DESIGNING MODIFICATIONS TO THE STRUCTURES/SYSTEMS

(75) Inventors: Gary E. Georgeson, Federal Way, WA (US); Morteza Safai, Seattle, WA (US); William T Edwards, Foristell, MO (US)

(73) Assignee: The Boeing Company, Chicago, IL (US)

(*) Notice: Subject to any disclaimer, the term of this patent is extended or adjusted under 35 U.S.C. 154(b) by 0 days.

(21) Appl. No.: 11/352,118

(22) Filed: Feb. 10, 2006

(65) Prior Publication Data

US 2007/0189454 A1  Aug. 16, 2007

(51) Int. Cl.  
*G01N 23/04* (2006.01)  
*G01N 23/201* (2006.01)

(52) U.S. Cl. .......................... 378/57; 378/87
(58) Field of Classification Search ............. 378/57–60, 378/86, 87; 700/182; 706/919–923  
See application file for complete search history.

(56) References Cited

U.S. PATENT DOCUMENTS

| | | | |
|---|---|---|---|
| 4,107,563 A | | 8/1978 | Oddell |
| 4,577,337 A | | 3/1986 | Light |
| 5,181,234 A | | 1/1993 | Smith |
| 5,243,665 A | * | 9/1993 | Maney et al. ............. 382/152 |
| 5,260,982 A | * | 11/1993 | Fujii et al. ............... 378/87 |
| 5,438,605 A | | 8/1995 | Burke et al. |
| 5,729,620 A | * | 3/1998 | Wang ...................... 382/128 |
| 5,763,886 A | * | 6/1998 | Schulte .................... 250/358.1 |
| 5,923,573 A | * | 7/1999 | Hatanaka .................. 703/2 |
| 6,094,472 A | * | 7/2000 | Smith ..................... 378/86 |

(Continued)

FOREIGN PATENT DOCUMENTS

DE  3142349  5/1983

(Continued)

OTHER PUBLICATIONS

Huifen, et al., Feature-based collaborative design, 2003, Elsevier, Journal of Materials Processing Technology, vol. 139, pp. 613-618.*

(Continued)

*Primary Examiner*—Edward J Glick  
*Assistant Examiner*—Anastasia Midkiff  
(74) *Attorney, Agent, or Firm*—The Boeing Company; Yee & Associates

(57) ABSTRACT

A method and system of determining the physical dimensions and configuration of a structure or system as a precursor to the design of modifications of the structure or system by analyzing hidden objects within the structure or system is provided. The method includes accessing the structure or system prior to the modification for preparation of the modification; scanning the structure or system with an x-ray backscatter unit; collecting data from the x-ray backscatter unit and combining and reconstructing the data into a 2-D, 2-D panoramic or 3-D data set; producing surfaces and structures of the hidden objects from the data set; and tying the surfaces and structures of the hidden objects into a pre-existing coordinate system of the structure or system creating a 3-D model.

15 Claims, 2 Drawing Sheets

U.S. PATENT DOCUMENTS

| | | | |
|---|---|---|---|
| 6,282,260 B1 * | 8/2001 | Grodzins | 378/87 |
| 6,292,533 B1 | 9/2001 | Swift et al. | |
| 6,370,222 B1 * | 4/2002 | Cornick, Jr. | 378/57 |
| 6,424,695 B1 | 7/2002 | Grodzins et al. | |
| 6,546,072 B1 | 4/2003 | Chalmers | |
| 6,560,315 B1 | 5/2003 | Price et al. | |
| 6,618,465 B2 | 9/2003 | Mohr et al. | |
| 6,637,266 B1 | 10/2003 | Froom | |
| 6,735,279 B1 * | 5/2004 | Jacobs et al. | 378/86 |
| 6,757,353 B2 * | 6/2004 | Furze | 378/58 |
| 6,888,640 B2 * | 5/2005 | Spina et al. | 356/601 |
| 6,950,719 B2 * | 9/2005 | Landers et al. | 700/182 |
| 7,069,192 B1 * | 6/2006 | Freitag | 703/1 |
| 7,086,028 B1 * | 8/2006 | Davis et al. | 716/11 |
| 7,103,434 B2 * | 9/2006 | Chernyak et al. | 700/98 |
| 7,218,704 B1 | 5/2007 | Adams et al. | |
| 7,280,990 B2 * | 10/2007 | Turner et al. | 706/45 |
| 7,305,063 B2 | 12/2007 | Heuscher | |
| 2001/0016803 A1 * | 8/2001 | Sartiono et al. | 703/1 |
| 2001/0021241 A1 * | 9/2001 | Swift et al. | 378/57 |
| 2002/0080913 A1 * | 6/2002 | Roder | 378/22 |
| 2002/0123812 A1 * | 9/2002 | Jayaram et al. | 700/98 |
| 2003/0043964 A1 | 3/2003 | Sorenson | |
| 2003/0204285 A1 * | 10/2003 | Thomas et al. | 700/182 |
| 2004/0086078 A1 * | 5/2004 | Adams et al. | 378/57 |
| 2004/0264626 A1 | 12/2004 | Besson | |
| 2005/0117701 A1 * | 6/2005 | Nelson et al. | 378/87 |
| 2006/0018434 A1 | 1/2006 | Jacobs et al. | |
| 2006/0043310 A1 * | 3/2006 | Arsenault et al. | 250/393 |

FOREIGN PATENT DOCUMENTS

| | | | |
|---|---|---|---|
| EP | 1227316 | | 7/2002 |
| JP | 04309187 A | * | 10/1992 |
| JP | 2006040053 A | * | 2/2006 |
| WO | WO 00/33059 | | 6/2000 |
| WO | WO 2007/129249 | | 11/2007 |

OTHER PUBLICATIONS

Wang, et al., Geometry-based semantic ID for persistent and interoperable reference in feature-based parametric modeling, 2005, Elsevier, Computer-Aided Design, vol. 37, pp. 1081-1093.*

Sanami et al., A Proposal of Assembly Model Framework Specialized for Unified Parametrics, 10th International Comference on Precision Engineering, Yokohama, Japan, Jul. 18-20, 2001, Tokyo University of Agriculture and Technology Kitajima Laboratory, pp. 962-966.*

Basak, et al., A Feature Based Parametric Design Program and Expert System for Design, 2004, Association for Scientific Research: Mathematical and Computational Applications, vol. 9, No. 3, pp. 359-370.*

Alan R. Crews et al., X-Ray Computed Tomography for Geometry Acquisition, Mar. 1993, Materials Directorate, Wright Laboratory, Air Force Materiel Command, Wight-Patterson Air Force Base; National Technical Information Service; Published In: US.

Zhu et al.; "X-ray Compton backscattering techniques for process tomography: imaging and characterization of materials"; Measurement Science and Technology; Mar. 1, 1996; vol. 7, No. 3, pp. 281-286; XP020063979; Institute of Physics Publishing; Bristol; UK.

Yancey; "CT-Assisted Reverse Engineering for Aging Aircraft Resupply"; Mar. 1998; XP002441957.

International Search Report and the Written Opinion of the International searching Authority (EPO) dated Jul. 30, 2007 on the corresponding PCT application (PCT/US2007/003466).

International Search Report on related PCT application (PCT/US2007/010843) from International Searching Authority (EPO) dated Dec. 12, 2007.

Written Opinion on related PCT application (PCT/US2007/010843) from International Searching Authority (EPO) dated Dec. 12, 2007.

Shedlock et al, "Optimization of an RSD x-ray backscatter system for detecting defects in the space shuttle external tank thermal foam insulation", Penetrating Radiation Systems and Applications VII. Edited by Doty, F. Patrick; Barber, H. Bradford; Roehrig, Hans. Proceedings of the SPIE, vol. 5923, pp. 205-216 (2005).

Non-Final Office Action on co-pending U.S. Appl. No. 11/744,115 dated Apr. 15, 2008.

Lockwood et al, "Field Tests of X-ray Backscatter Mine Detection", Detection of Abandoned Land Mines, 1998. Second International Conference on the (Conf. Publ. No. 458) Edinburgh, UK Oct. 12-14, 1998, London, UK, IEE, UK, Oct. 12, 1998, pp. 160-163, XP006505028, ISBN: 0-85296-711-X.

Poranski et al, "X-ray Backscatter Tomography for Nondestructive evaluation at the Naval Research Lab", Proc SPIE Int Soc Opt Eng; Proceedings of SPIE—The International Society for Optical Engineering 1995 Society of Photo-Optical Instrumentation Engineers, Bellingham, WA, USA, vol. 2459, 1995, pp. 70-78, XP002462304.

International Search Report on related PCT application (PCT/US2007/010785) from International Searching Authority (EPO) dated Jan. 10, 2008.

Written Opinion on related PCT application (PCT/US2007/010785) from International Searching Authority (EPO) dated Jan. 10, 2008.

Notice of Allowance on co-pending U.S. Appl. No. 11/744,115 dated Jan. 13, 2009.

Non-Final Office Action on co-pending U.S. Appl. No. 11/739,835 dated Sep. 5, 2008.

Final Office Action on co-pending U.S. Appl. No. 11/744,115 dated Sep. 16, 2008.

Notice of Allowance on co-pending U.S. Appl. No. 11/739,835 dated Nov. 24, 2008.

* cited by examiner

SYSTEM AND METHOD FOR DETERMINING DIMENSIONS OF STRUCTURES/SYSTEMS FOR DESIGNING MODIFICATIONS TO THE STRUCTURES/SYSTEMS

BACKGROUND OF THE INVENTION

1. Field of the Invention

The present invention relates to determining the physical dimensions and configuration of structures and/or systems as a precursor to the design of modifications to structures and/or systems, and more particularly, determining the physical dimensions and configuration of the structures and/or systems by analyzing hidden objects utilizing X-ray backscatter technology.

2. Background

There is a very large market for modification of structures and/or systems, especially military and commercial aircraft. The greatest challenge faced by modification designers is uncertainty about the geometrical configuration of a given structure and/or system, such as an aircraft. Often, the legacy data (drawings, planning, tooling) is insufficient to determine the present configuration of the product, resulting in significant costs for re-design of new systems being placed on the structure and/or system.

Conventional methods of determining configurations for modifying an aircraft have been the use of digital photographs, panoramic cameras, and line of sight reverse engineering technology. These methods have had only limited success in solving the problem due to the limited access to the aircraft. The time frame for modifications is relatively short. Currently, designers must wait until the structure and/or system can be partially disassembled before line of sight reverse engineering determination/verification of geometric configurations of hidden objects can be performed.

As a result, there is a high need for collecting geometrical definition data of hidden objects in structures and/or systems. A non line of sight reverse engineering method could significantly reduce the current engineering lead time incurred after an aircraft is interred. Therefore, what is needed is a method and system for determining the geometric configuration of the structure and/or systems for use in designing modifications, without having to remove parts of the structure before designing the modification.

SUMMARY OF THE PRESENT INVENTION

In one aspect of the present invention, a method of determining the physical dimensions and configuration of a structure and/or system as a precursor to the design of modifications of the structure and/or system by analyzing hidden objects within the structure and/or system is provided. The method includes accessing the structure and/or system prior to the modification for preparation of the modification; scanning the structure and/or system with an x-ray backscatter unit; collecting data from the x-ray backscatter unit and combining and reconstructing the data into a 2-D, 2-D panoramic and/or 3-D data set; producing surfaces and structures of the hidden objects from the data set; and tying the surfaces and structures of the hidden objects into a pre-existing coordinate system of the structure and/or system creating a 3-D model.

In another aspect of the present invention, an inspection system for analyzing hidden objects within a structure and/or system for modification is provided. The system includes an X-ray backscatter system for collecting data about the hidden objects; a computing system for combining and reconstructing the data into a 2-D, 2-D panoramic, and/or 3-D data set and producing surfaces and structures from the data set; and a display connected to the computer system for displaying the surfaces of the objects and/or systems of the structure.

This brief summary has been provided so that the nature of the invention may be understood quickly. A more complete understanding of the invention can be obtained by reference to the following detailed description of the preferred embodiments thereof in connection with the attached drawings.

BRIEF DESCRIPTION OF THE DRAWINGS

The foregoing features and other features of the present invention will now be described with reference to the drawings of a preferred embodiment. In the drawings, the same components have the same reference numerals. The illustrated embodiment is intended to illustrate, but not to limit the invention. The drawings include the following Figures.

DETAILED DESCRIPTION OF THE PREFERRED EMBODIMENTS

The following detailed description is of the best currently contemplated modes of carrying out the invention. The description is not to be taken in a limiting sense, but is made merely for the purpose of illustrating the general principles of the invention, since the scope of the invention is best defined by the appended claims.

According to the present invention, a method of determining the physical dimensions and configuration of a structure and/or system using non-line of sight reverse engineering by analyzing hidden objects of the structure and/or system is provided. Although the method of the present invention is implemented using an aircraft, those skilled in the art will recognize that the principles and teachings described herein may be applied to a variety of structures and/or systems with hidden objects, such as power plants, processing plants, refineries and transportation systems, including, but not limited to, automobiles, ships, helicopters, and trains.

Figure 1:
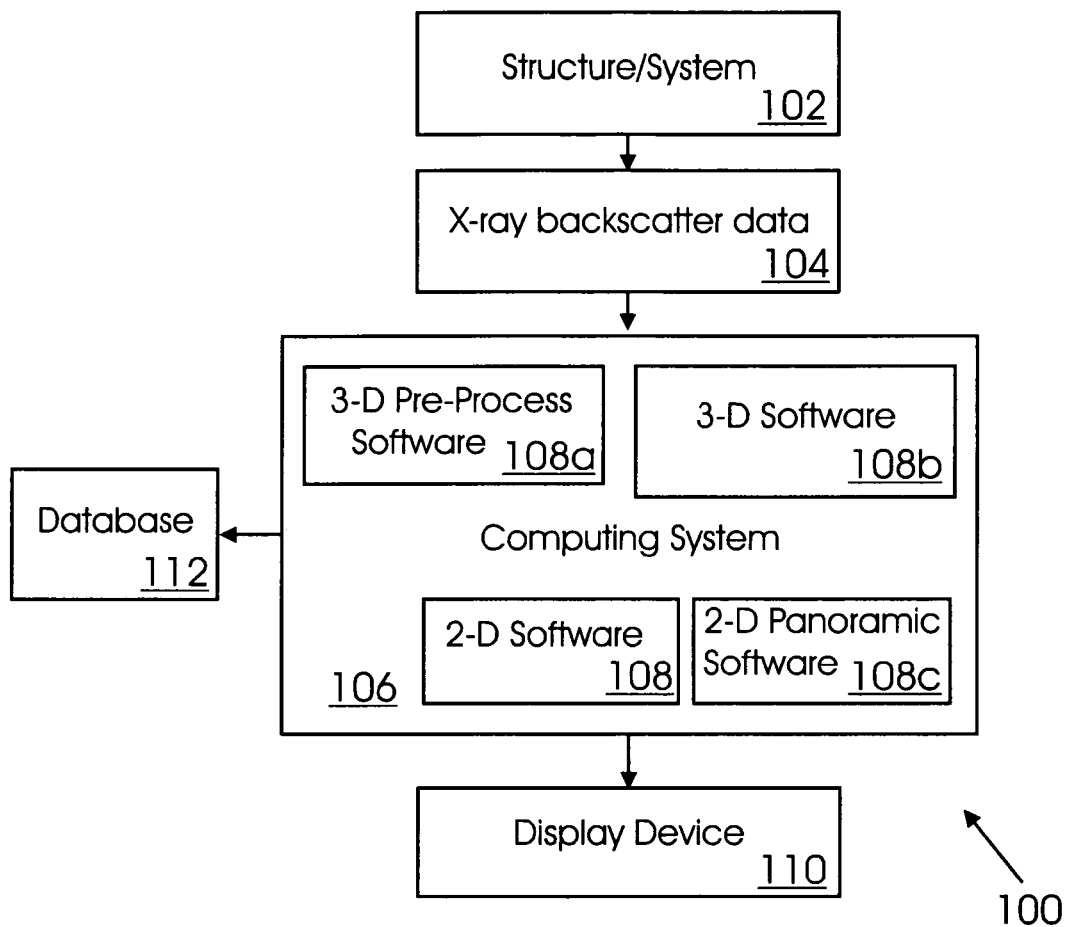
FIG. 1 illustrates a top-level block diagram of a system using the method of determining the physical dimensions and configuration of a structure and/or system using non-line of sight reverse engineering by analyzing hidden objects of the structure and/or system, according to one aspect of the present invention.

Turning to FIG. 1, a block diagram of a system 100 using the method of determining the physical dimensions and configuration of a structure and/or system 102 using non-line of sight reverse engineering by analyzing hidden objects of structure and/or system 102 is illustrated. System 100 utilizes conventional X-ray backscattering technology to capture and display 2-D, 2-D panoramic and 3-D geometric information of the hidden objects of structure and/or system 102, such as an aircraft. Structure and/or system 102 is inspected using a conventional X-ray backscatter unit.

The X-ray backscatter unit electronically generates X-rays to examine an object and/or system by capturing data 104 from X-ray photons that are scattered from the objects and/or systems undergoing inspection and produces characteristic shadow-like images similar to medical X-rays. A technician uses the X-ray backscatter unit to scan the interior of an aircraft that is scheduled for modification. Scanning can be done from either the inside or the outside of the aircraft with a modified X-ray backscatter instrument that "sees" the hidden objects behind the walls of the aircraft. The X-ray backscatter instrument is modified so that the instrument can move within the structure and/or system, for example installing tracks in the structure and/or system. Furthermore, the instrument is modified so it can take multiple imaging to capture 2-D, 2-D panoramic and/or 3-D models and have more than one position to be able to maneuver around the seat or other objects in the airplane. (The X-ray energies can be lower if the scanning is from the inside, since the transmitted beam does not have to penetrate the skin.) Fiducials of known dimensions and/or depth may be placed in the region of the X-ray shot in order to supplement accurate dimensional and depth information. Existing structure and/or system definition information may be used as parameters for reconstructing the collected data into 2-D, 2-D panoramic, and/or 3-D data sets.

The X-ray backscatter unit (or "system") can be utilized by laying a track down on the inside of the aircraft and putting the system on the track so that an X-ray source puts out X-rays from the inside the aircraft. Some of the X-rays will scatter back and detectors pick up the scattered X-rays and produce an image of the interior of the aircraft without having to take the panels off. Alternatively, if the aircraft is large enough, the X-ray backscatter inspection system can be placed in a vehicle, such as a van, and the vehicle is driven directly into the aircraft.

Data 104 is taken from at least one position along the aircraft and from at least one orientation relative to the aircraft. Then the data is sent to computing system 106 having conventional 2-D software 108 that utilizes a superimposing algorithm to generate projected 2-D images of the surfaces of the objects of the aircraft. In one alternative, 2-D images 104 from conventional 2-D software 108 can be stitched together using conventional 2-D panoramic image creation software 108c to create a spherical immersive image. Alternatively, 3-D pre-process software 108a constructs a 3-D data point set of the structure and/or system from the collected data 104 and conventional 3-D software 108b that digitally reconstructs the 3-D point data into 3-D surfaces that define the hidden objects. Finally, the generated data are stored in a database 112 and displayed on a display device 110, such as a monitor or liquid crystal display, for data collectors to view.

Typically, the cabling, wiring, tubing and the structure of the aircraft itself along with the relative location of all objects and/or systems are displayed. Energy information from the scattered X-rays can also be used to distinguish between material types (i.e. aluminum vs. plastic pipe) and possibly even system contents (i.e. water line versus air).

Figure 2:
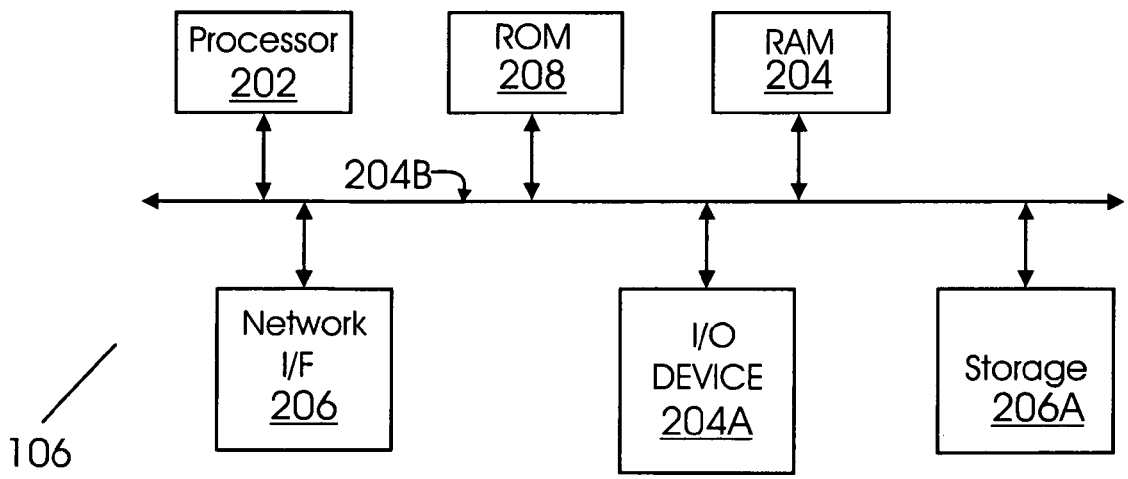
FIG. 2 shows a block diagram of the internal architecture of a typical computing system utilized in one aspect of the present invention.

FIG. 2 shows a block diagram of a typical computing system 106 (may also be referred to as a host computer or system) utilized in a preferred embodiment of the present invention. Computing system 106 includes a central processing unit ("CPU") (or microprocessor) 202 connected to a system bus 204B. Random access main memory ("RAM") 204 is coupled to system bus 204B and provides CPU 202 with access to memory storage 206A for storing the generated image. When executing program instructions, CPU 202 stores those process steps in RAM 204 and executes the stored process steps out of RAM 204.

Host system 106 connects to a computer network (not shown) via network interface 206 (and through a network connection (not shown)). One such network is the Internet that allows host system 106 to download applications, code, documents and others electronic information.

Read only memory ("ROM") 208 is provided to store invariant instruction sequences such as start-up instruction sequences or basic Input/output operating system (BIOS) sequences.

Input/Output ("I/O") device interface 204A allows host system 200 to connect to various input/output devices, for example, a keyboard, a pointing device ("mouse"), a monitor, printer, a modem and the like. I/O device interface 204A is shown as a single block for simplicity and may include plural interfaces to interface with different types of I/O devices.

It is noteworthy that the present invention is not limited to the architecture of the computing system 106 shown in FIG. 2. Based on the type of applications/business environment, computing system 106 may have more or fewer components. For example, computing system 106 can be a set-top box, a lap-top computer, a notebook computer, a desktop system or other types of systems.

Figure 3:
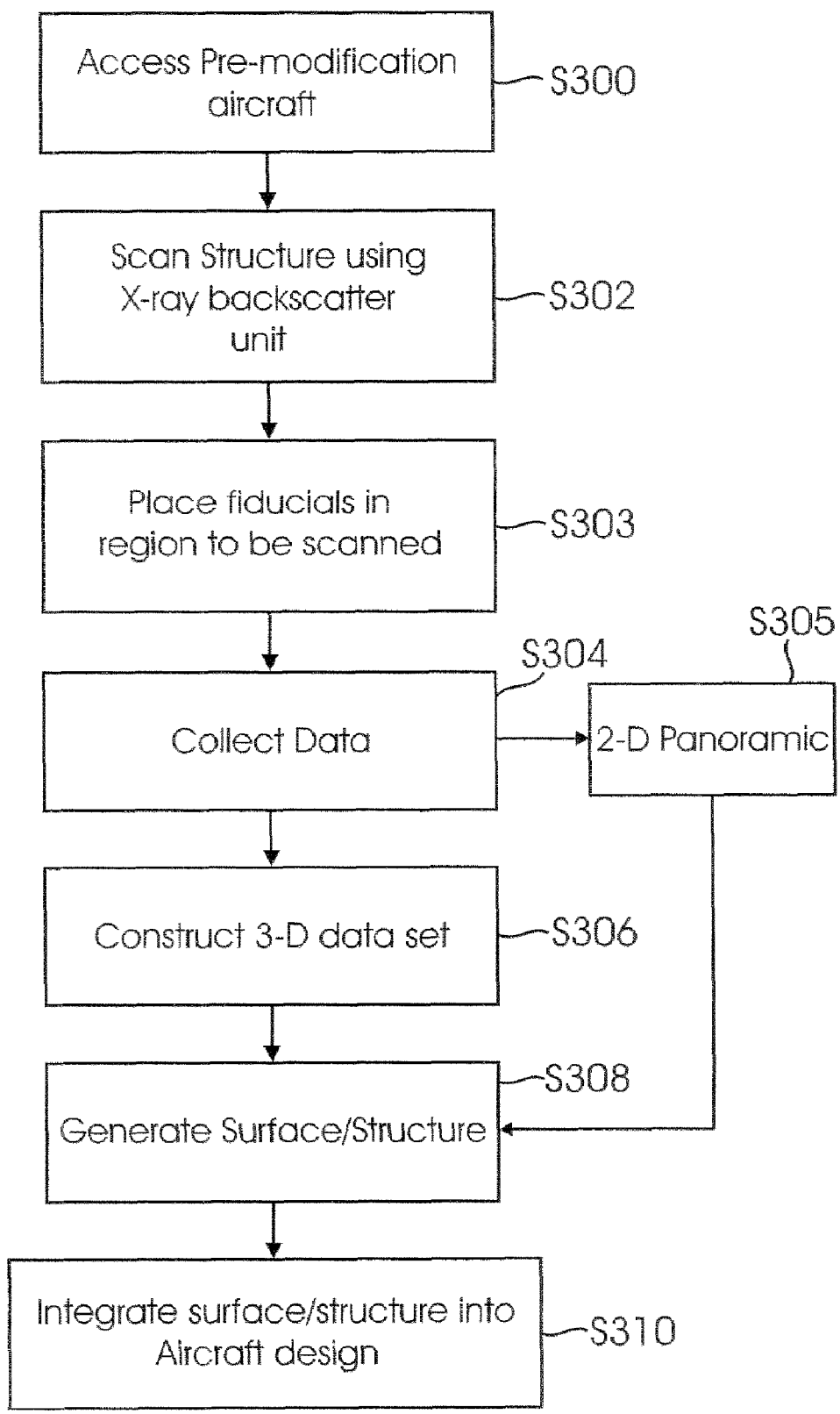
FIG. 3 is a flow chart illustrating the steps of determining the physical dimensions and configuration of a structure and/or system using non-line of sight reverse engineering by analyzing hidden objects of the structure and/or system, according to one aspect of the present invention.

Turning to FIG. 3, a flow chart illustrating the steps of determining the physical dimensions and configuration of an aircraft using non-line of sight reverse engineering by analyzing hidden objects of the aircraft, according to a preferred embodiment of the present invention, is shown. The method begins in step S300 when access is provided to an aircraft that is to undergo X-ray backscatter imaging. The walls and ceiling of the aircraft are scanned with the X-ray backscatter unit in step S302. In step S300, fiducials of known dimensions and/or depth are optionally placed in the structure and/or system in order to supplement accurate dimensional depth information. Typically, only one to five days of access is needed for data collection. After the data collection is completed, the aircraft is returned to service until its scheduled modification. The data is collected in step S304. In one alternative in step S305, 2-D images 104 from conventional 2-D software 108 can be stitched together using conventional 2-D panoramic image creation software 108c, such as Panoweaver and Ipix, to create a spherical immersive image. Alternatively, in step S306, a 3-D data point set of the structure and/or system is constructed from the collected data 104, using 3-D software 108a in computing system 106.

Next, in step S308, conventional 3-D software 108b, for example Innovmetric Polyworks or Raindrop Geomagic, digitally reconstructs the 3-D point data into 3-D surfaces that define the hidden objects. Finally, in step S310, the 3-D surfaces are translated into a structure and/or system reference coordinate system. The generated 3-D surfaces can then be used like traditional engineering data, by combining them with other models to form a 3-D CAD model of the complex structure and/or system. Design engineers use the 3-D model of the hidden structures to plan the routing and installation of hardware and systems. Once the aircraft is available for modification, the walls and insulation are removed from the aircraft and the hardware is installed as designed the first time, without the need for costly re-design. The model is saved in the database for any future modifications.

It is noteworthy that the 3-D images produced by reconstruction backscatter X-rays can be produced in a variety of ways including, but not limited to, (1) orienting collimators to collect scattered X-rays coming from several known orientations; (2) using multiple detectors that are collimated to only register X-rays coming from specific directions; (3) a flying spot detector; (4) upgrading a 2-D scan system (such as the AS&E z-backscatter system) to scan along the length of the aircraft with the sources and fanned collimators oriented in different directions; and (5) making multiple passes of the aircraft while changing the orientation of the source and fanned collimator.

Although the present invention has been described with reference to specific embodiments, these embodiments are illustrative only and not limiting. Many other applications and embodiments of the present invention will be apparent in light of this disclosure and the following claims.

What is claimed is:

1. A method of determining the physical dimensions and configuration of a structure or system comprising:
   scanning a structure or system with an x-ray backscatter unit;
   collecting data from x-ray photons scattered by the structure or system;
   combining and reconstructing the collected data into a 2-D, 2-D panoramic or 3-D data set;
   generating 3-D representations of hidden objects from the data set;
   mapping the 3-D representations of the hidden objects into a structure or system reference coordinate system;
   combining the 3-D representations mapped into the reference coordinate system with models to form a 3-D CAD model of the scanned structure or system; and
   designing modifications to the structure or system using the 3-D CAD model by planning routing and installation of hardware in the structure or system.

2. The method of claim 1, wherein the structure or system is an aircraft, an automobile, a building, a ship, a helicopter, a launch platform, a power plant, an oil rig, or an oil refinery.

3. The method of claim 1, further comprising accessing the structure or system prior to a modification, wherein the modification is fully designed prior to the structure or system being available for modification.

4. The method of claim 1, wherein the data set comprises 2-D, 2-D panoramic or 3-D geometric information data.

5. The method of claim 1, wherein the structure or system is scanned from the inside.

6. The method of claim 1, wherein the structure or system is scanned from the outside.

7. The method of claim 1, wherein the data is taken from at least one position along the structure or system.

8. The method of claim 1, wherein the data is taken from at least one orientation relative to the structure or system.

9. The method of claim 1, wherein fiducials of known dimensions or depth are optionally placed in the structure or system in order to supplement accurate dimensional and depth information.

10. An inspection system for analyzing hidden objects within a structure or system for a modification, comprising:
    an X-ray backscatter system for scanning the structure or system and collecting data about hidden objects within the structure or system; and
    a computing system for combining and reconstructing the data into a 2-D, 2-D panoramic or 3-D data set, generating 3-D representations of the hidden objects from the data set, mapping the 3-D representations of the hidden objects into a structure or system reference coordinate system, combining the 3-D representations tied into the reference coordinate system with models to form a 3-D CAD model of the scanned structure or system, and designing modifications to the structure or system using the 3-D CAD model by planning routing and installation of hardware in the structure or system.

11. The system of claim 10, wherein the data collected by the X-ray backscattering unit is 2-D, 2-D panoramic and 3-D geometric information.

12. The system of claim 11, wherein pre-existing drawings of the structure or system are used as parameters for creating a 2-D, 2-D panoramic or 3-D model from the collected data sets.

13. The system of claim 12, further comprising a database connected to the computing system for storing the collected data for future use.

14. The system of claim 10, wherein fiducials of known dimensions and depth are placed in the structure or system in order to supplement accurate dimensional and depth information.

15. The system of claim 10, further comprising:
    a display connected to the computing system for displaying the representations of the hidden objects of the structure or system.

* * * * *